(12) United States Patent
Leahy et al.

(10) Patent No.: US 8,679,078 B2
(45) Date of Patent: *Mar. 25, 2014

(54) OCULAR DRUG DELIVERY DEVICE

(71) Applicant: Vista Scientific LLC, Andover, MA (US)

(72) Inventors: Charles D. Leahy, Concord, MA (US); Denis Labombard, Georgetown, MA (US)

(73) Assignee: Vista Scientific LLC, Andover, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/621,362

(22) Filed: Sep. 17, 2012

(65) Prior Publication Data

US 2013/0023838 A1    Jan. 24, 2013

Related U.S. Application Data

(63) Continuation of application No. 12/841,357, filed on Jul. 22, 2010, now Pat. No. 8,287,504, which is a continuation of application No. 10/569,743, filed as application No. PCT/US2004/027510 on Aug. 25, 2004, now Pat. No. 8,167,855.

(60) Provisional application No. 60/497,831, filed on Aug. 26, 2003.

(51) Int. Cl.
A61M 35/00    (2006.01)

(52) U.S. Cl.
USPC ............................... 604/294; 604/289

(58) Field of Classification Search
USPC ................................................ 604/289, 294
See application file for complete search history.

(56) References Cited

U.S. PATENT DOCUMENTS

| | | |
|---|---|---|
| 3,416,530 A | 12/1968 | Ness |
| 3,618,604 A | 11/1971 | Ness |
| 3,828,777 A | 8/1974 | Ness |
| 3,845,201 A | 10/1974 | Haddad et al. |
| 3,867,519 A | 2/1975 | Michaels |
| 3,962,414 A | 6/1976 | Michaels |

(Continued)

FOREIGN PATENT DOCUMENTS

| | | |
|---|---|---|
| EP | 0262893 | 4/1988 |
| EP | 0923918 | 6/1999 |

(Continued)

OTHER PUBLICATIONS

D. Lisa Land, et al.; "Sizes and Shapes of Conjunctival Inserts"; ICLC, vol. 21 Nov./Dec. 1994; pp. 212-217.

(Continued)

*Primary Examiner* — Michele M Kidwell
(74) *Attorney, Agent, or Firm* — Leason Ellis LLP

(57) ABSTRACT

An ocular device for insertion into an eye is provided and includes a body having an anterior surface and a posterior surface for placement on one of superior sclera and inferior sclera of the eye. The posterior surface is defined by a base curve that is substantially identical to a radius of curvature of the one of the superior sclera and inferior sclera of the eye. In one embodiment, the ocular device serves as an ocular drug delivery device and contains an active pharmaceutical agent, a lubricant, etc.

9 Claims, 7 Drawing Sheets

(56) References Cited

U.S. PATENT DOCUMENTS

| | | |
|---|---|---|
| 3,963,025 A | 6/1976 | Whitaker et al. |
| 3,993,071 A | 11/1976 | Higuchi |
| 3,995,635 A | 12/1976 | Higuchi |
| 4,014,335 A | 3/1977 | Arnold |
| 4,135,514 A | 1/1979 | Zaffaroni et al. |
| 4,164,559 A | 8/1979 | Miyata et al. |
| 4,179,497 A | 12/1979 | Cohen et al. |
| 4,186,184 A | 1/1980 | Zaffaroni |
| 4,190,642 A | 2/1980 | Ben-Dor |
| 4,343,787 A | 8/1982 | Katz |
| 4,592,752 A | 6/1986 | Neefe |
| 4,730,013 A | 3/1988 | Bondi et al. |
| 4,863,457 A | 9/1989 | Lee |
| 5,137,728 A | 8/1992 | Bawa |
| 5,147,647 A | 9/1992 | Darougar |
| 5,322,691 A * | 6/1994 | Darougar et al. ............. 424/427 |
| 5,472,436 A | 12/1995 | Fremstad |
| 5,660,851 A | 8/1997 | Domb |
| 6,217,896 B1 | 4/2001 | Benjamin |
| 6,413,245 B1 | 7/2002 | Yaacobi et al. |
| 6,413,540 B1 | 7/2002 | Yaacobi |
| 6,416,777 B1 | 7/2002 | Yaacobi |
| 6,669,950 B2 | 12/2003 | Yaacobi |
| 6,713,081 B2 | 3/2004 | Robinson |
| 6,808,719 B2 | 10/2004 | Yaacobi |
| 6,986,900 B2 | 1/2006 | Yaacobi |
| 7,094,226 B2 | 8/2006 | Yaacobi |
| 2004/0176749 A1 | 9/2004 | Lohmann |
| 2005/0013845 A1 * | 1/2005 | Warren et al. ................ 424/430 |
| 2005/0181018 A1 | 8/2005 | Peyman |
| 2008/0145406 A1 | 6/2008 | Asgharian et al. |
| 2008/0171072 A1 | 7/2008 | Burczynski |

FOREIGN PATENT DOCUMENTS

| | | |
|---|---|---|
| EP | 1473003 | 11/2004 |
| JP | Hei 6-273702 A | 9/1994 |
| JP | Hei 11-151263 A | 6/1999 |
| WO | WO 01/32140 | 5/2001 |
| WO | WO 03/020172 | 3/2003 |

OTHER PUBLICATIONS

Marco Fabrizio Saettone; :Solid Polymeric Inserts/Disks as Drug Devices; Biopharmaceutics of Ocular Drug Delivery; pp. 61-79.

* cited by examiner

OCULAR DRUG DELIVERY DEVICE

CROSS REFERENCE TO RELATED APPLICATIONS

This application is a continuation of U.S. patent application Ser. No. 12/841,357, filed Jul. 22, 2010, which is a continuation of U.S. patent application Ser. No. 10/569,743, filed Nov. 9, 2006 (now U.S. Pat. No. 8,167,855), which is a national stage of PCT/US04/27510, filed Aug. 25, 2004, which claims the benefit of U.S. patent application Ser. No. 60/497,831, filed Aug. 26, 2003, each of which is hereby incorporated by reference in its entirety.

STATEMENT REGARDING FEDERAL SPONSORSHIP

The U.S. Government has a paid-up license in this invention and the right in limited circumstances to require the patent owner to license others on reasonable terms as provided for by the terms of Grant No. 2 R44 EY 13479.02 awarded by the National Institute of Health.

BACKGROUND

Due to the blood-aqueous and blood-retina barriers, it is difficult to get medicines administrated via the systemic route into the eye itself. Doses large enough to overcome these barriers often result in unacceptable systemic side effects. Virtually all acute and chronic disease of the eye are therefore treated with medication in the form of topical eye drop formulations that are applied at least once per day.

In addition to being difficult for patients to insert accurately, the use of eye drops suffers from two major technical disadvantages, their rapid elimination from the eye and their poor bioavailability to the target tissues. As a result of tear film dilution and elimination and the permeability barriers of the cornea, typically less than five percent of the applied dose of drug reaches the intraocular tissues. Topical ophthalmic pharmaceutical solutions are therefore formulated in high concentrations and require frequent dosing. Non-compliance with treatment, due to required frequency of dosing, lack of detectable symptom relief in immediate association with treatment application, undesirable systemic side effects due to the need for high concentrations of drug and other reasons, is a major clinical disadvantage.

The idea of placing a solid device into or near the eye to deliver a drug or a lubricant over time is not new. Most recent scientific interest in this field stems from advances in surgical techniques, pharmacology and pharmacokinetics, as well as the availability of improved polymer systems that can be tailored to the specific needs of ocular drug delivery. For clarity, the distinction should be made between a device that is "inserted into the eye", meaning placed under the eyelids, external to the eyeball itself, and traditionally referred to as an "ocular insert", vs. a device that is inserted into the eye surgically, meaning an intraocular insert placed inside the eyeball, or partly inside the eyeball itself. In fact, some devices are implanted in the layers of connective tissue forming the globe of the eyeball, and may even extend through these layers into the eyeball. And some that could be inserted topically under the eyelids could also be surgically implanted under the outermost layer, the conjunctiva, anteriorly, or Tenon's capsule, posteriorly, and would correctly be referred to as subconjunctival or sub-Tenon's inserts. This would be done via a minimally invasive procedure that does not open into the eyeball itself, but rather into the space currently utilized by ophthalmologists for subconjunctival or sub-Tenon's injections.

Saettone concisely stated the case for ophthalmic inserts as set forth in the following points: (Saettone, in Chapter 4, *Biopharmaceutics of Ocular Drug Delivery*, Edman P, ed., CRC Press, London, 1993, 61-79.).

1. Increased ocular permanence with respect to standard vehicles, hence a prolonged treatment activity and a higher drug bioavailability
2. Accurate dosing (all of the drug is theoretically retained at the absorption site)
3. Possible reduction of systemic absorption, which occurs freely with standard eye drops via the nasal mucosa.
4. Better patient compliance resulting from a reduced frequency of medication and a lower incidence of visual and systemic side effects
5. Possibility of targeting internal ocular tissues through non-corneal (conjunctival-scleral) penetration mutes
6. Increased shelf life with respect to eye drops, due to the absence of water
7. Possibility of providing a constant rate of drug release Prior art has concerned itself with fitting a device under the eyelid into the conjunctival potential space. The goal to date has been to retain the device in this potential space, or potential pocket, formed by the palpebral portion of the conjunctiva (lining the inside of the eyelid) and the bulbar portion of the conjunctiva (lining the outside of the front half of the eyeball). The deeper parts of this potential pocket are the loose folds of the conjunctiva referred to as the conjunctival formix or conjunctival cul-de-sac. This potential pocket of continuos tissue is limited by the eyelid margins, near the eyelashes, and the corneal limbus, the circle forming the border of the cornea with the white of the eye. It is referred to as potential space because it not particularly "designed" to hold anything normally, but rather the excess tissue allows movement of the eyeball in the orbit and retains foreign bodies and the tear film from going behind the eyeball into the head or brain. Being a soft, mucus membrane tissue, the conjunctiva easily swells in response to allergens or infection. The space it occupies is therefore potentially expandable by its outward pressure on the eyelids.

Devices meant to be inserted into this potential space have many shapes and sizes, and are often designed from the engineering standpoint of ease of manufacture (Land D, Benjamin W., Sizes and Shapes of Conjunctival Inserts. ICLC. 21: November/December 212-217, 1994). Resulting shapes are simple, such as oblong rectangular, cylindrical, etc. Their sizes and shapes are predicated on the art of tablet manufacture and the desire to be inconspicuous in situ. That is, comfort and retention in the conjunctival sac is attained by slipping something into the pocket formed by the conjunctiva lining the eyeball and the inside of the eyelid, and presuming it would be tolerated by the subject by virtue of its small size. This lack of design specific to the limiting contours of the intended space leads to discomfort and ejection of devices of any significant volume. This limitation of overall dimensions in turn significantly restricts the amount of drug they are able to contain and consequently deliver. An example of a commercially produced ocular insert for drug delivery is found in the subject of U.S. Pat. No. 3,618,604, the Ocusert®, assigned to Alza Corporation. This product was designed from an engineering standpoint of making a drug-releasing "sandwich". Adequate retention and comfort were assumed by virtue of its small size. Several subsequent patents assigned to Alza Corporation (U.S. Pat. Nos. 3,416,530, 3,828,777) also describe devices that are designed to improve drug delivery kinetics based primarily on material characteristics. These patents address design only in that the devices are "adapted for insertion in the cul-de-sac of the conjunctiva between the sclera of the eyeball and the lower lid, to be held in place against the eyeball by the pressure of the lid". Although they are in fact quite small in comparison to the present invention, significant problems in retention and irritation with the use of the Ocusert® devices are reported in the literature (Sihvola P, et al. Practical Problems in the Use of Ocusert-Pilocarpine Delivery System. Acta Ophthalmol. (Copenh.), 58 (6) 933-937, 1980). In fact, the products have recently been discontinued, having never been widely accepted or used clinically.

Another example of prior art that utilizes the potential space of the conjunctival cul-de-sac is that of Benjamin in U.S. Pat. No. 6,217,896. Benjamin, noting the failure to do so in the prior art, proposes to maximize the use of the actual volume and shape that could be contained in the cul-de-sac, addressing improved conformity, larger drug capacity and increased stability within the sacs. His design is a result of maximally filling the potential space of the conjunctival cul-de-sac with a molding material, and describing the resulting shape obtained. Although his design description includes a back curvature conforming somewhat to the bulbar surface, this results from his approach of maximizing the volume and shape that could be contained in the human conjunctival sac. The features that he describes as unique to his design are those of the dimensions and volume of the expanded sac itself: "a crescent shape horizontally; a thick inferior horizontal ridge and a wedge-like shape sagittally". The lack of well-defined mathematical dimensions or expressions for the design, or even a consistent recommended relationship between the back curvature and the bulbar surface, confirm his approach of molding the potential space by expanding it with molding material. As with other prior art, his invention is not designed to fit the eyeball itself and fits the potential space as an empirically derived molded design. Pulling the eyelid away from the globe would result in the insert sliding out of correct position or orientation and/or falling out of the eye.

Another example of prior art that includes a back curvature conforming to the bulbar surface also pursues the engineering approach of fitting a device into the potential space under the eyelid rather than fitting the eyeball itself. In U.S. Pat. No. 3,416,530, Ness describes an "Eyeball Medication Dispensing Tablet". The hollow chamber of this patent is quite small, in order to comfortably fit in the cul-de-sac.

Much of the prior art depends on material flexibility to achieve retention, without specifying the material of the device or any values or ranges for the flexibility claimed. In WO 01/32140 A1 to Darougar, flexibility is claimed in claim 1 as being sufficient to allow bending along the curvature of the eye within the upper or lower formix upon being positioned, such that the device does not extend onto any visible portion of the eyeball. The flexibility of Darougar et al is intended to allow entrapment of a long, thin device in the conjunctival folds of the formix, and specifically excludes contact with the eyeball. The scope of the design of our invention allows incorporation of materials of any flexibility.

It is important to note that, other than Benjamin in U.S. Pat. No. 6,217,896, the history of the art of ocular inserts for drug delivery has been one of creating small devices, designed to be inconspicuous to the wearer while being trapped in the folds of the conjunctiva or between the eyelid and the globe. This has been addressed primarily by virtue of small size, and secondarily by virtue of shape. Special design features for stability consist of anchors to assist in entrapment, such as the protrusions mentioned in some prior art, such as WO 01/32140 A1 to Darougar, where the protrusions are quite small and are proposed as anchors to assist in entrapment of a long, thin rod-shaped device and render it undetectable in the conjunctival folds of the formix. Examples of prior art of considerably small volumes include the Ocusert® described above and the subject of U.S. Pat. No. 3,828,777, which measures at most 5.7×13.4 mm on its axes and 0.5 mm in thickness, yielding 38.5 µl volume. EPA-0262893 to Darougar discloses a rod-like ocular insert device having a volume of 17 µl. These restrictions on volume significantly limit the amount and subsequent duration of practical drug delivery to the eye.

When reviewing the prior art it is evident that the need exists for an ocular device that is both stable and comfortable in the eye, yet has the volume and mass to deliver therapeutic agents at a controlled rate over an extended period of time.

SUMMARY

The present invention in a first aspect provides an ocular device adapted for the controlled sustained release of a therapeutic agent upon application onto the upper or lower sclera of the eye, said device designed to fit the sclera of the eye. The ocular device comprises an elongated body of a polymeric material said body containing a pharmaceutically active ingredient or a lubricant. The ocular device is fitted to the scleral curvature within the upper or lower formix, upon being positioned so that the longitudinal axis of said device is generally parallel to the transverse diameter of the eyeball, said device being of a size and configuration such that, upon insertion into the upper or lower conjunctival area the device does not extend onto any normally visible portion of the eyeball, i.e., the palpepral aperture. The posterior surface of the device corresponds in a prescribed manner to the shape of the sclera, in a manner similar to how the posterior surface of a corneal contact lens corresponds in a prescribed manner to the shape of the cornea. The posterior edge of the ocular device can be tapered with a radius and a degree of edge lift in a manner similar to the edges of a corneal contact lens. The anterior surface can be designed to interact with the eyelid shape, tension and movement as the device occupies the anatomical potential space beneath the eyelid, in order to provide appropriate positioning, stability, movement and comfort.

The ocular devices of this invention have been designed to be stable in the eye and therefore well retained over a prolonged period of time. Additionally, the ocular devices are also designed to provide the patient with levels of comfort and tolerance not achieved with ocular inserts. The increased comfort, stability and retention of the ocular devices, fitted in the upper or lower conjunctival areas, can be used to deliver therapeutic agents to the eyes via continuous treatment for extended periods of time. One application of the device could be used for the singular or periodic treatment or prevention of inflammation, infection or allergy. Repeated applications for up to one to three months or longer each can be used for chronic diseases, such as glaucoma. The device may be fitted and removed by the ophthalmic technician, nurse or doctor, as well as by the patients themselves, following a brief lesson similar to that utilized for contact lens wear.

The ocular device is designed to be placed on the upper or lower conjunctiva, well within the junction of the palpebral conjunctiva of the upper or lower eyelid and the bulbar conjunctiva covering the sclera of the eyeball. Relative to the bulbar conjunctiva, the devices of this invention maintain their orientation, and exhibit only minimal movement vertically or laterally, by the pressure and movement of the eyelid against the eyeball, or by the movement of the eyeball itself. Slight movement of the device with blinking and eye movement is advantageous, as with contact lenses, to prevent adherence of the device to the eye and the associated entrapment of metabolic debris and deposits. Such movement relevant to the eyeball of a corneal contact lens is often referred to as "lag".

The device may include raised areas, acting in use to maintain position and stability and minimize random movement of the device within the conjunctival area, preferably two raised areas each positioned so as to be symmetrically disposed about the center point of the body of the device.

The ocular device of this invention is designed to fit the sclera of the eye, which has a radius of about 11 mm to about 13 mm. Surprisingly, this radius in the adult population is relatively constant at about 12 mm Therefore, the device has an overall, base curve radius of from about 11 mm to about 16 mm. Preferably, the device base curve radius is 12 to 14 mm. In general, for adults, the area of the sclera limited by the upper formix is greater than the area of the sclera limited by the lower formix. Thus, an ocular device of the present invention with a length of up to 35 mm may remain on the upper sclera and one with a length of up to 25 mm may remain on the lower sclera without causing discomfort.

The length of the device of this invention is conveniently from 8 to 35 mm for use on the superior sclera to suit the eyes of different sizes such as infants, children and adults, or from 8 to 25 mm for use on the inferior sclera to suit the eyes of different sizes such as infants, children and adults.

The width (height of the vertical meridian with the device on the eye) of the device of this invention is preferably from about 1.0 mm to 14.0 mm to suit the eyes of different sizes such as those of infants, children and adults. The edge of the device of this invention is preferably tapered and more preferably includes elements of the anterior and posterior peripheral surface, such as peripheral curve widths and radii and a resultant edge lift and an edge apex contour to optimize comfort and eyelid interaction.

The volume of the device of this invention can range from about 70 microliters to about 400 microliters and is preferably from about 100 microliters to about 200 microliters for adults. Infants and children under age five may require a device with a volume below 100 microliters.

BRIEF DESCRIPTION OF THE DRAWING FIGURES

Certain preferred embodiments and modifications thereof will become apparent to those skilled in the art from the detailed description herein having reference to the figures that follow, of which:

DETAILED DESCRIPTION OF PREFERRED EMBODIMENTS

The present invention incorporates principles that have some basis in rigid gas permeable and soft corneal contact lens design and more particularly, the engineering of ocular devices, according to the present invention, is particularly suited for producing devices for drug delivery to the eye while being fitted to the sclera (white) of the eye. Accordingly and as described in great detail below, the device designs described herein address a back central curvature, peripheral curves, edge apex contour, edge lift, overall shape and thickness profile corresponding to the features of and delimiting aspects of the superior and inferior sclera, such as the scleral surface curvature, extraocular muscle insertion points, corneo-scleral junction contour, and the corresponding eyelid interaction. In complete contrast to prior art devices and drug delivery approaches, the present ocular devices are specifically designed to fit the sclera of the eye, with the overall fitting contour accounting for the limiting anatomical features and landmarks of the sclera, such as the extraocular muscle insertions and limbal junction with the cornea. The devices are held in place by fluid attraction, and the devices interact with the eyelids, as does a contact lens, for movement, positioning, stability and comfort. The posterior contour allows comfortable relative apposition to the scleral surface, and allows movement with blinking and eye movement. The anterior contour, edge design and the thickness profile of the embodiments of this invention interact with the eyelid both during and between blinks to optimally orient the device in a stable and comfortable position on the sclera. Each device is inserted by placing it on the inferior or superior anterior sclera (white) of the human eye or in treatment of primates and quadrupeds, as a contact lens is typically placed on the clear cornea. The design of the device does not require insertion into the conjunctival cul-de-sac for retention. The design allows the device to remain in place even if the eyelid is retracted, just as a contact lens remains in place when the eye is open. This design can be utilized in its embodiments with a wide range of drugs, lubricants and other medicinal agents, and with a wide range of potential eroding and non-eroding drug delivery materials or combinations of materials, such as via polymer matrix chemistry or reservoir systems. The polymeric material of the device may be any polymer that is above its gas transition at 35° C. For example, a silicone elastomer, acrylate, and methacrylate compositions and hydrogels are suitable. The mechanisms of the therapeutic agent or lubricant release may be, for example, by diffusion through the matrix of the device, by diffusion through an outer wall of the device, osmosis and bioerosion. The design of the device allows large volumes of drug to be delivered over a long duration.

Figure 1:
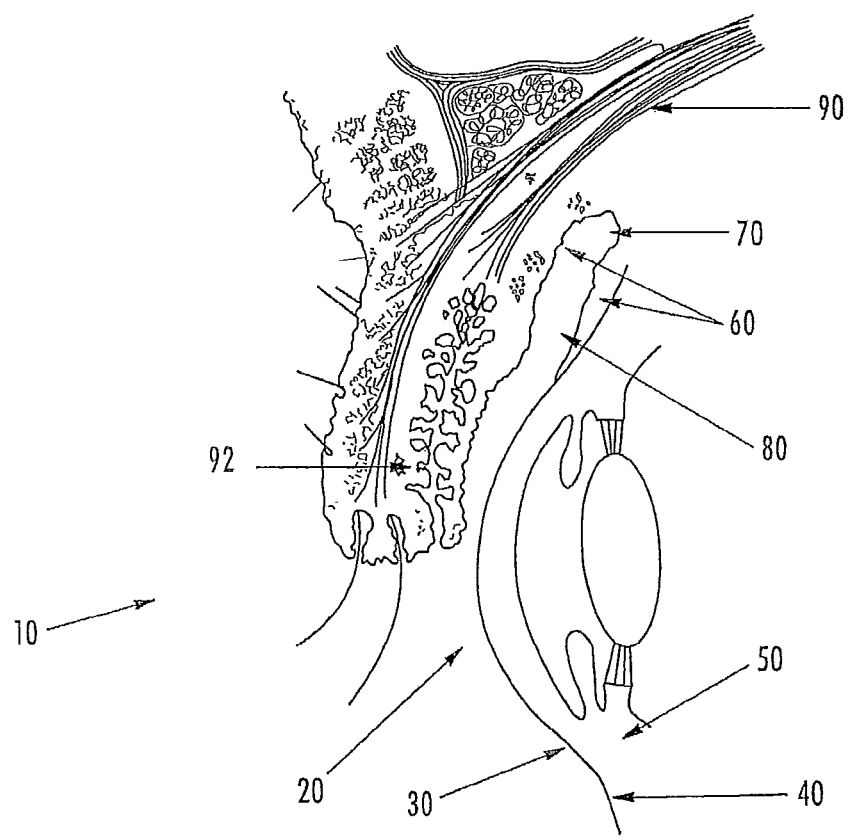
FIG. 1 is a diagrammatic sectional view of an eye and eyelid.

With reference to FIG. 1, the following definitions and terms may be useful regarding the anatomy of the anterior eyeball and the description of the details of the invention. When describing the eye, it is convention to describe it by using a number of different established anatomical terms. FIG. 1 shows an eye 10 that includes a cornea 20 which is the transparent anterior portion of the eyeball and has a steeper curvature than the rest of the eyeball. The corneal limbus 30 describes an annular border zone between the cornea 20 and the bulbar conjunctiva 40 and the sclera 50. The conjunctiva 60 refers to the mucous membrane extending from an eyelid margin to the corneal limbus 30, forming the inner layer of the eyelids and an anterior outer layer of the eyeball. The conjunctival formix 70 is the loose, free conjunctiva connecting the eyelid (palpebral) and eyeball (bulbar) portions of the conjunctival cul-de-sac 80 which is the potential space between the bulbar and palpebral conjunctivae and in the conjunctival formix that can expand into a real space by insertion of a device or other object or substance. The palpebral conjunctivae are supported by the various muscles 90 and embedded glands 92 of the eyelid. As previously mentioned, the sclera 50 is the white, opaque outer tunic of the eyeball which covers it entirely except for the segment covered anteriorly by the cornea 20. The sclera 50 is in turn covered anteriorly by the conjunctiva 60.

Figure 2:
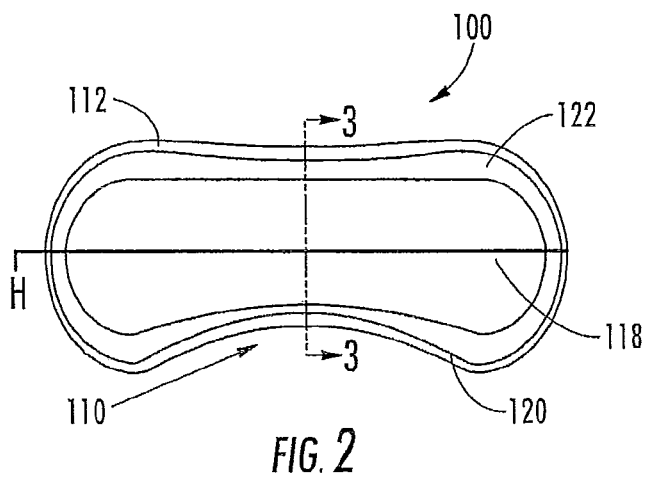
FIG. 2 is a front elevation view of an ocular drug delivery device according to a first embodiment.
Figure 3:
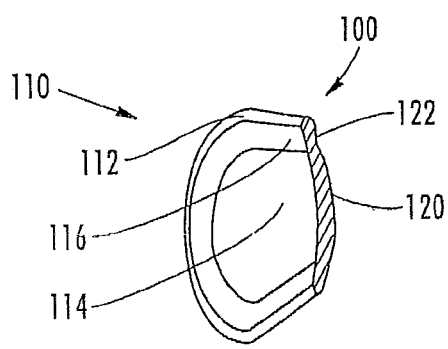
FIG. 3 is a cross-sectional view taken along the line 3-3 of FIG. 2.

With reference to FIGS. 1-3, FIGS. 2 and 3 generally illustrate an ocular drug delivery device 100 that embodies the features of the present invention and is constructed for insertion into and wear in the eye 10 by placing it on the inferior or superior anterior sclera (white) 50 of the human eye 10 or in treatment of primates and quadrupeds. The device 100 is initially set forth in FIG. 2 in order to define a number of design terms that help describe the structure and function of all of the present ocular drug delivery devices. Thus, it will be understood and will become more apparent below that the device 100 is merely one exemplary embodiment of the present invention and in no way is to be construed as limiting the scope of the present invention. The device 100 includes a body 110 that has an edge apex contour 112 which is the amount and positioning of rounding of the device edges and is typically defined as a radius profile swept around a perimeter of the device 100. The device 100 has a base curve 114 which is defined as the primary radius in each meridian i.e. vertical (axis 3-3) and horizontal (axis H-H), and is the surface of the device 100 that is in contact with the sclera 50 (the posterior surface of the device). In the case where the values in each meridian are the same, the base curve 114 is defined as a spherical base curve. In the case where the values in each meridian are different, the posterior surface is defined as a toric posterior surface. The device 100 also has an edge lift 116 which is a sectional geometry width around the perimeter adjacent to and following the edge apex contour 112 where the base curve 114 is flatter (increased). The edge lift 116 is defined by the incremental radius increase and by a width.

A front curve(s) 118 is defined as the secondary device radius in each meridian i.e. vertical and horizontal (axes defined along the body 110). The front curves generate the surface that is in contact with the lid (the front surface of the device). In the case where the values in each meridian are the same, the front curve 118 is defined as a spherical. In the case where the values in each meridian are different, the front surface of the device 100 is defined as a tonic front surface. In a preferred embodiment, the present device 100 disclosed herein, the front curves 118 are defined as tonic. The device 100 also includes splines 120 which are geometric entities created by polynomial equations, which define smooth blended contour surfaces bridging from one defined shape or cross-section to another. A lenticular 122 is a manipulation of the thickness of the edge of the device 100 at the front curve geometry adjacent to the edge apex contour 112 on the eyelid side of the device 100. A lenticular 122 can be a positive or a negative curve and typically has a reversed radius direction to the primary front curve radius geometry and the lenticular 122 follows the profile of the edge apex contour 112, thus providing a reduced thickness cross-section profile around the perimeter of the device 100.

The body 110 of the device is constructed and configured to fit the contours of the white part (sclera 50) of the eyeball itself, while paying tribute to the effects of the eyelids on the position, stability, movement and comfort of the device 100. This fit can be analogized to the design and fitting of a corneal contact lens over the contours of the cornea 20. While the primary function of the contact lens is to optically correct a refractive error, the lens must also be designed to be comfortable, stable and non-irritating, and to remain in place in order to function successfully. Although remaining in place, it also must retain a slight movement with eyelid movement and a slight lag behind movement of the eyeball. This is to permit tear film circulation around the lens to prevent redness, irritation, adherence to the tissue and build-up of mucus and other surface deposits on the anterior or posterior surfaces. Similarly, an ocular device, such as device 100, for drug delivery also must exhibit stability of position and yet would preferably retain slight movement and lag for the same reasons. It also cannot cause excessive awareness or create discomfort as wearing time proceeds. The interaction with the lid is also determined by the design, and, as with a contact lens, will affect the position, stability, movement and comfort of the device 100. Proper interaction of the device 100 with the eyelid also allows flow of the tear film around the device 100, which helps keep it clean of mucous build-up that tends to occur with foreign bodies that are simply trapped in the conjunctival cul-de-sac 80.

Figure 4:
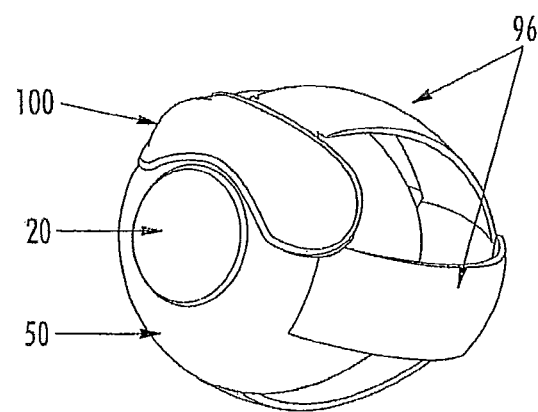
FIG. 4 is a perspective view of an eye with the device of FIG. 1 fitted to the superior sclera.
Figure 5:
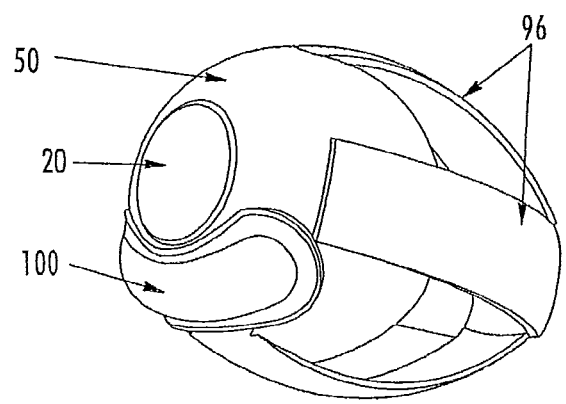
FIG. 5 is a perspective view of an eye with the device of FIG. 1 fitted to the inferior sclera.

The device 100 of this invention can be worn over the sclera 50 superior to the cornea 20 as shown in FIG. 4 or inferior to the cornea 20 as shown in FIG. 5. It will therefore be appreciated that all of the ocular drug delivery devices embodying the principals and features of the present invention can be positioned in either of these two locations and can be marked as such.

Contact lens fit and retention depends on the attraction of the device to the eye by the surface tension of the tears (fluid attraction), and is assisted by the curvature of the back of the contact lens. Typically a contact lens has a back curvature corresponding (according to relationships known to those in the art) to that of the cornea, so that the lens has a preference for being attracted to the surface of the cornea as opposed to the sclera, or white part of the eye. The general attraction of the contact lens to the eye is evidenced by the fact that a contact lens does not simply fall out if the wearer tilts the head down while the eyes are open.

The attraction of the contact lens to a specific part of the eye (the cornea 20) is evidenced by the observation that, with the eye wide open, the lens moves with the eye, such as left, right, up or down with change of gaze direction. This preferential attraction of the contact lens to a particular part (shape) of the eyeball, specifically, the more steeply curved cornea 20 vs. the more flat sclera 50, can be demonstrated if the eye is held open wide and a soft contact lens is dragged from the cornea 20 to the white part 50 of the eye, leaving only a small portion remaining over the cornea 20. The contact lens will drift back onto the cornea 20 on its own without a blink as long as the eye remains wet enough. This is because the contact lens is specifically designed, by the series of posterior base (central) and peripheral curves and the diameter, thickness, etc., to position in close relationship to the cornea 20. In sum, the design and intent of contact lens wearing is to position the contact lens over the cornea 20 and there is absolutely no teaching or suggestion of placement of the contact lens in another anatomical area of the eye 10. In fact, the contact lens is not suitable for placement in other areas, including the sclera 50 specifically.

Thus, contact lens design and wear is in complete contrast to the present invention, where the device 100 is designed to fit the contours and anatomical features of the white part 50 of the anterior eye, in order to remain in position on the sclera 50. Currently available contact lenses, although designed with several desirable attributes of ocular devices for drug delivery, such as adequate comfort, retention and movement, do not provide significant drug delivery capability. This is due to the inability of the lens materials to deliver drug for significantly long duration. Most studies investigating contact lenses pre-soaked in drug solutions show release of all of the drug in a matter of hours or perhaps one to two days. The constraints of the contact lens materials available having adequate optical clarity (for vision) and oxygen permeability (required for adequate metabolism in the avascular cornea) do not allow high priority in material choice of polymers that offer extended drug delivery. Thus, previous drug delivery design which focuses on mimicking a contact lens design suffers from a number of disadvantages.

The invention disclosed herein is specifically designed to fit the non-corneal (scleral) anterior surface of the eyeball, remaining outside the visual axis and off of the avascular cornea. Therefore, optical design, optical clarity and oxygen permeability are not constraining parameters to the materials that can be used with the design comprising this invention. The device 100 is constructed to be retained at the non-corneal anterior ocular surface for the topical delivery of drug to the eye. Contrary to existing ocular drug delivery thought in terms of the mechanism of topical drug delivery, the present device 100 is specifically designed to fit the sclera 50 of the eye 10. This is evidenced by the fact that each embodiment of the present device 100 stays on the sclera 50 even if the eyelid is pulled away from the eye 10, similar to how a contact lens stays on the cornea 20 while the eye is wide open. This is a different approach than that of conventional ocular drug delivery design that relies on entrapment of the device in the folds of the conjunctival sac or between the eyelid and the globe for its retention in position. However, along with retention, the term "fit" in the contact lens field also encompasses positioning, stability, movement, eyelid interaction and even comfort. As with contact lens designs, there are specific design features that render the device 100 described in this application capable of performing adequately in all these aspects of "fit". Due to its design to fit the sclera 50 of the eye 10 and account for dynamic interaction with the movement of the eye 10 and of the eyelid, the present device 100 provides comfort in a large design. The total device volume can be much greater than device volume in much of the prior art, which is significantly limited by that size which creates detectable sensation or discomfort.

The ocular devices of this invention, in their simplest form, are designed to fit the sclera 50 of the eye. Generally, most of the devices include a body that has a generally overall oval shape where the horizontal dimension is greater than the vertical dimension. This is depicted in the embodiment shown in FIGS. 6-8, where an exemplary ocular device 200 is provided. The ocular device 200 has a body 202, a first end 203 and an opposing second end 205 as well as an anterior surface 207 and an opposing posterior surface 209 that are closest to one another along a peripheral edge 211 of the body 202.

It is preferred that the shape be symmetrical about a medial axis (vertical meridian) that extends across the width of the body 202 (e.g., line 7-7 of FIG. 6), such that the lateral halves are mirror images. This aspect allows for the same device design to be used in the right and left eyes (in the same orientation), and on the superior or inferior sclera 50 of eye 10. A base curve 212 radius of the device 200 is chosen to fit the sclera 50. As best shown in FIG. 7, the body 202 has a thickness that is less at its edges 211 and greater toward and including the middle of the body 202. More specifically, the body 202 can be designed such that it has a maximum thickness at the middle thereof as measured from each of the side edges of the body 202 and as a result, the maximum thickness generally lies along the line 8-8 (horizontal meridian) of FIG. 6. One will appreciate that as a result of this configuration, the thickness of the device 200 continually increases from each side edge toward the middle of the body 202.

Figure 8:
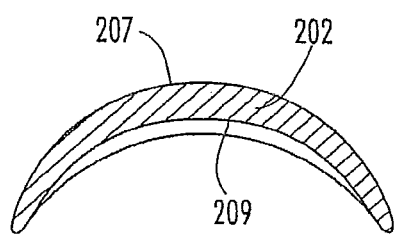
FIG. 8 is a cross-sectional view taken along the line 8-8 of FIG. 6.

In addition, the cross-sectional thickness of the body 202 from the first end 203 to the opposing second end 205 is likewise not uniform but instead tapers inwardly toward each end 203, 205 from the central section (middle) of the body 202, as best shown in FIG. 8. In terms of a maximum cross-sectional thickness of the body, as measured longitudinally from the first end 203 to the second end 205, this generally lies along the line 8-8 of FIG. 6. The body 202 thus tapers in the longitudinal direction from its central region toward the ends 203, 205 such that the distance between the anterior surface 207 and the posterior surface 209 is at a greatest in the central region, while is at a minimum at the ends 203, 205 and more particularly along the peripheral edge 211 of the body 202. The edge thickness, measured along the perimeter edge 211, of the body 202 is generally uniform along the entire perimeter of the elliptical body 202 where the anterior surface 207 and the posterior surface 209 meet. Accordingly, this body design is characterized as being a significant tonic shape on a fairly spherical base curve with a uniform edge radius. In one exemplary embodiment the device 200 can have the following dimensions: the width can range from about 10 mm to about 25 mm, the height is about 5 mm to about 12 mm and the cross-sectional thickness (center thickness) is from about 1.0 mm to about 3.0 mm as measured through the center of the body 202, i.e., along line 7-7 of FIG. 6. The base curve radius of the device 200 is from about 12 mm to about 14 mm When the device 200 has the above dimensions, the volume ranges from about 72 µl to about 400 µl. It will be appreciated that the aforementioned dimensions are merely exemplary in nature and do not serve to limit the present invention in any way since it is possible for the device 200 to have one or more dimensions that lie outside of one of the above ranges but still be completely operable as an ocular delivery device.

As previously mentioned, the present inventors discovered that the device 200 is particularly suited for and is in face constructed and configured for placement on the either the superior sclera as shown in FIG. 4 or the inferior sclera as shown in FIG. 5. Not only is the device 200 comfortable to wear in these locations but also it delivers the aforementioned advantageous drug delivery properties that were otherwise not achievable in conventional ocular devices that were inserted into the eye 10 and worn at locations other than the sclera 50, such as the cornea 20.

FIGS. 9-12 illustrate an ocular drug delivery device 300 according to a second embodiment of the present invention. The ocular drug delivery device 300 shares a number of similarities to the device 200, such as both being intended for placement on the sclera 50; however, there are a number of differences in terms of the construction and design of the device 300 compared to the device 200. Similar to the device 200, the device 300 has a degree of symmetry in that the device 300 has a body 302 that is preferably symmetric about a central axis that is defined as being equidistant from a first end 304 and an opposing second end 306 of the body 302 and extending between the two sides of the body 302. This central axis (vertical meridian) is depicted as line 11-11 in FIG. 9. As with the device 200, the device 300 includes an anterior surface 301 as well as a posterior surface 303.

Figure 9:
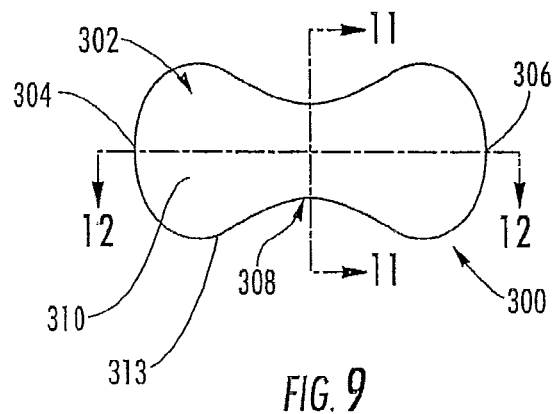
FIG. 9 is a front elevation view of an ocular drug delivery device according to a third embodiment.
Figure 10:
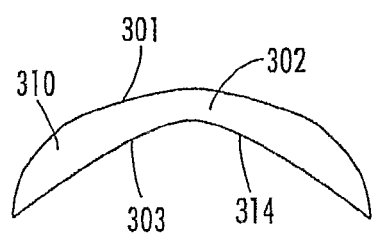
FIG. 10 is a top plan view of the device of FIG. 9.
Figure 11:
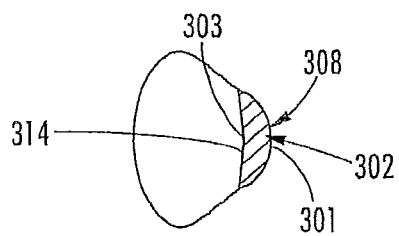
FIG. 11 is a cross-sectional view taken along the line 11-11 of FIG. 9.
Figure 12:
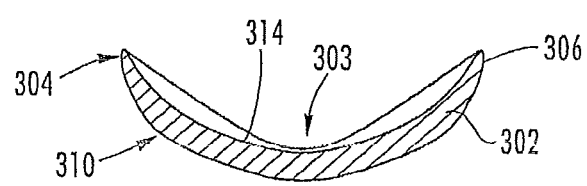
FIG. 12 is a cross-sectional view taken along the line 12-12 of FIG. 9.

As best seen in the front elevation view of FIG. 9, the device 300 generally takes the form of a "dumbbell" with a relatively thin central section 308 and two opposing lobe sections 310 formed at ends 304, 306, respectively. The central axis aspect ratio of the lobe 310 to the central section 308 (vertical meridian 11-11, as viewed from the front elevation view of FIG. 9) can vary from about 2:1 to about 10:1. In theory, the central portion 308 could be infinitely narrow and thin, but increasingly negative effects on stability and comfort would occur as such dimensions were approached and therefore, the above ranges, while not limiting, serve as a guideline for yielding a suitable device 300. The dumbbell shape of the device 300 redistributes the mass away from the center 308 towards the ends 304, 306 of the device 300, and leads to desired positioning on the sclera 50 under the lid and greater stability on the eye 10 while maintaining volume.

Increasing the mass in the periphery of the device 300 also takes advantage of greater scleral surface area available in the forty-five degree quadrants vs. the central axis (superior and inferior), which are limited by the extraocular muscle insertions (superior or inferior recti muscles). The larger shape of the lobes 310 relative to the central portion 308, the greater height of the lobes 310 from the surface of the eye and the surface contour of the lobes 310 all contribute to the proper positioning, stability and movement of the device 300 on the sclera 50. Although the lobes 310 can be of any geometrically shaped perimeter, for optimal interaction with the eyelid and the blink process, the perimeter of the lobes 310 distal to the central connecting portion 308 generally has a rounded appearance as viewed in the top plan view of FIG. 9, and can have parabolic shapes at the ends 304, 306 with splines between them. The lobes 310 can be from about 0.5 mm to about 20 mm at their greatest diameter. More preferred is a diameter from about 3 mm to about 17 mm. Most preferably, the lobes 310 can be from about 7 mm to about 13 mm at their greatest diameter. The center thickness, as measured from the anterior surface 303 to the posterior surface 301 (similar to the same measurement in a contact lens) of the central portion 308 of the device 300 can range from about 0.50 mm to about 4.0 mm, more preferably from about 0.10 mm to about 2.0 mm, and most preferably from about 0.10 mm to about 1.25 mm, while a thickness, measured across a central section, of the lobe 310 can range from about 0.5 mm to about 5.0 mm, more preferably from about 0.5 mm to about 3.0 mm, to avoid visible bulging through the eyelid, and most preferably from about 0.5 min to about 2.5 mm. The greater thickness and volume of the lobes 310 compared to other regions of the body 302 retains adequate volume for clinical quantities of drug delivery while maintaining position and stability on the eye through interaction with the eyelid. Keeping the thickness profile of the central portion 308 below that of the lobes 310 decreases the potential volume available, but offers significant benefits in position, stability, appearance (no bulge noted through eyelid) and comfort in the use of the device 300. The nasal and temporal perimeter ("ends") 304, 306 of the lobes 310 can approximate circular, parabolic or elliptical shapes. The transitional curves between the central portion 308 of the device 300 and each of the lobes 310 can be linear, parabolic, elliptical or hyperbolic, with splines being preferred, blending to a central cross-section at line-line 12-12. The overall horizontal width of the device 300 can range from about 10 mm to about 25 mm, with a base curve radius 314 from about 12 mm to about 14 mm. The overall volume of the device 300 ranges from about 70 µl to about 400 µl. The thickness of the device 300 tapers down to a defined minimum, mostly uniform edge thickness around the entire edge perimeter 313.

The symmetry of the device 300 about the vertical meridian (axis 11-11 (vertical meridian)) is such that the lateral halves are mirror images. This aspect allows for the same device design to be used in the right and left eyes (in the same orientation) and on the superior or inferior sclera 50 of the eye 10.

Figure 13:
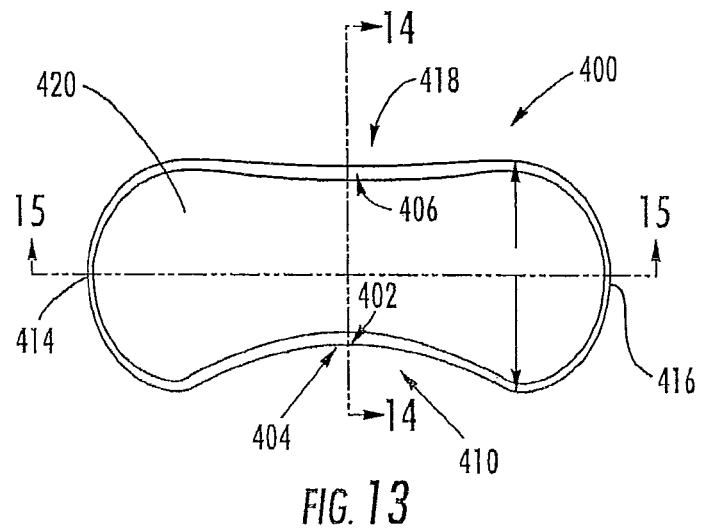
FIG. 13 is a front elevation view of an ocular drug delivery device according to a fourth embodiment.
Figure 14:
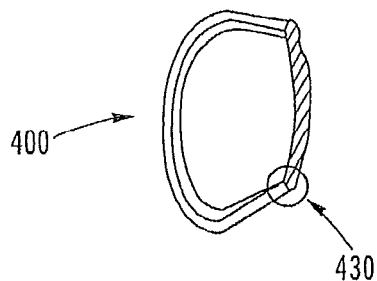
FIG. 14 is a cross-sectional view taken along the line 14-14 of FIG. 13.
Figure 15:
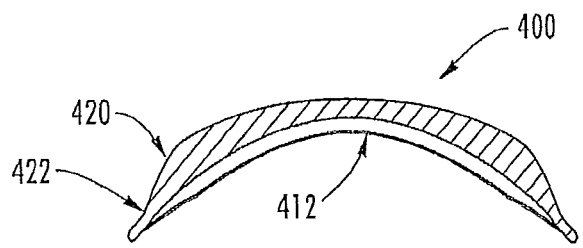
FIG. 15 is a cross-sectional view taken along the line 15-15 of FIG. 13.

In yet another embodiment that is illustrated in FIGS. 13-15, an ocular drug delivery device 400 is provided. In a number of intended applications, the embodiment of device 400 is preferred over the other prior embodiments (devices 200 and 300) for the reasons set forth above. More specifically, the device 400 is designed to better fit the anatomical features of the eye 10. In this embodiment of the invention, an edge 402 of a central portion 404 thereof that is proximal to the cornea 20 during placement on the eye 10 has a shape corresponding approximately to a projection of the corneal perimeter. This inwardly curved shape has a curvature such that if you projected the corneal boundary (at the limbus) and the device 400 boundary into a corneal plane, the device 400 would have an approximately uniform clearance in relation to the corneal boundary when the device 400 is in its intended position on the superior or inferior sclera 50. This feature is termed the "corneal relief curve" and is generally indicated at 410. The curvature of the corneal relief curve in this design is a conic or spline projection of the curvature of the junction of the corneal and sclera (the limbus). Most preferably, it follows a uniform offset radially from the limbus along the sclera 50. The height difference, as measured parallel to 14-14, due to this inward curvature of the central axis 14-14 (vertical meridian) between the center of the device 400 and lobe portions 420 can range from about 0.50 mm to about 3.5 mm, and more preferably, from about 0.50 mm to about 2.5 mm. The "relief contour" provides a shape that will not impinge on the sensitive corneal surface, thereby avoiding effects on comfort and potentially vision, and approximates a uniform clearance in relation to the cornea 20. The edge 406 of the central portion 404 distal to the cornea also has an inwardly curved shape, with a curvature allowing clearance of the insertion of the rectus muscle (superior or inferior, depending upon placement of the device on the superior or inferior sclera). This feature is termed a "muscle relief curve" and is generally indicated at 418. The height difference, due to this inward curvature, of the central axis 14-14 between the center of the device 400 and the lobe portions 420 can range from about 0.15 mm to about 2.5 mm, or more preferably, from about 0.15 mm to about 1.5 mm.

Symmetry about the center axis 14-14 (vertical meridian) in FIG. 13 is maintained in such an embodiment, allowing it to be worn inferiorly or superiorly in most cases, but the mass of the central portion 404 is greater on the side of the longitudinal meridian 15-15 of FIG. 13 that is distal to the cornea, so that in the superior position, the inward curvature 418 of the device 400 clears the superior rectus muscle insertion, but is less of an inward curvature than that 410 on the side proximal to the cornea.

The center thickness along line 14-14 (vertical meridian) varies from about 0.25 mm to about 3.0 mm according to one embodiment, a longitudinal length of the device 400 measured from end 414 to end 416 ranges from about 15 mm to about 22 mm, and the maximum vertical height (as viewed from the side elevation view of FIG. 14) ranges from about 5 mm to about 14 mm The distance at the center point across this central portion 404, from proximal to distal relief curves, along the axis 14-14, can vary from less than about 0.5 mm to about 12 mm More preferred is the range of from about 1 mm to about 10 mm. Most preferred is the range of from about 6 mm to about 10 mm. The centers of each dumbbell (each end lobes) 420 on either side of the central portion 404, can range in thickness from about 0.5 mm to about 5.0 mm, more preferablty, from about 0.5 mm to about 3.0 mm, to avoid visible bulging through the eyelid, and more preferably, from about 0.5 mm to about 2.5 mm. The lobes 420 can contain the greater part of the volume of the device 400, which ranges from about 70 µl to about 400 µl.

The base curve radius, generally indicated at 412, of the device 400 ranges from about 12 mm to about 14 mm.

Each end lobe 420 has a mid-peripheral section 422 that is thinner than the peripheral portion of each end lobe 420. This is to mimic the edge profile technique typically used in the geometry of a significantly high powered rigid contact lens. Such high powered lenses have been observed to be most likely of common clinical corneal contact lens designs to dislocate from the cornea, due to the interaction with the superior eyelid. The volume of such a contact lens is necessary to provide adequate optics for visual correction Similarly, the volume of the device 400 is necessary to provide adequate drug for release. In both cases, the lenticular feature is a benefit in maintaining position and stability, through interaction with the eyelid, of the device 400 that has sufficient volume. The lenticular feature yields a transition from a positive front apical curve of the lobe 420 being blended into a negative reverse curve in a range from about 0.5 mm to about 3.5 mm.

The symmetry of the device about the axis 14-14 (vertical meridian) is such that the lateral halves are mirror images. This aspect allows for the same device design to be used in the right and left eyes (in the same orientation) and on the superior or inferior sclera of an eye (by rotating 180 degrees in the corneal plane).

In all embodiments, the back surface approximates the primary scleral curvatures, at least in situ, depending on the flexibility of the material. The flexibility of the material utilized to form the device determines how closely the back surface must correspond to the scleral curvatures prior to insertion of the device. For example, in theory, a highly flexible material could be made with larger base curve radii, and could conform in use to form itself to the surface of the sclera. This is comparable to the "draping" effect of a soft contact lens on the eye.

The present invention utilizes conformation to the eyeball curvature to establish the fit against the surface of the eyeball, not to assist with entrapment in the conjunctival folds of the formix. The design of this invention aims to provide a surface geometry to fit the sclera 50 of the eye 10 in order to balance comfort and retention with a greater volume of the device to contain greater amounts of drug for longer delivery to the eye. Adjusting the base curvature and peripheral curvatures of the posterior surface of this invention allows the use of many materials with a wide range of flexibility. Such adaptation of design to materials properties is well known in the art of contact lens design. A range of spherical, aspheric and toric back surface base curves, in combination with various spherical, aspheric and toric peripheral curve systems, similar to those known in the art of contact lens design, provide the posterior surface that fits against the surface of the eyeball.

Therefore, although a flat posterior surface is within the range of possible posterior surfaces of this invention, the preferred range of volumes of the device of this invention would result in less of a draping effect and a more limited tendency to conform to the scleral surface if the posterior surface were flat prior to insertion in the eye, virtually regardless of material utilized. This is comparable to a thick soft contact lens, such as a high plus power lens used for the correction of aphakia, draping, flexing or bending less on the eye than a very thin, low power soft contact lens. It can be noted analogously that even a thin low power soft contact lens, which is quite flexible, is manufactured with a base curvature corresponding somewhat to the ocular (corneal) curvature, as opposed to a flat posterior surface, to assist with fitting and draping. In a preferred embodiment of this invention therefore, the device would have a posterior surface approximating the scleral curvature.

In fact, the surface of the anterior sclera forms a somewhat tone, asymmetric surface. This would be analogous to fitting a contact lens on the more asymmetrical mid-peripheral cornea, rather than basing the design on a central corneal topography. A back tonic design posterior aspheric surface contact lens would be applicable for use on such a tonic surface. A more preferred embodiment would therefore have a posterior surface with an aspheric shape or with two spherical radii that would allow it to conform to the scleral curvatures. Although potential drug delivery devices with a spherical back surface design would adequately approximate the scleral surface, the flattening and steepening of elliptical or aspheric back curvatures would allow fine tuning of the movement and tear flow, and hence the optimal fit of the device.

Another advantage of specific designs of the back surface of the device is to allow uniform tear film flow. More uniform tear flow would allow more constant release of the drug from the device to the eye. Therefore, although a tonic back surface is not necessary for the more flexible materials, it would be preferred for the positioning, stability, comfort, retention and uniform drug delivery with the more rigid materials. The most preferred embodiment of this invention therefore comprises a posterior surface with two elliptical radii that would allow it to conform to the slightly elliptical scleral surface. These elliptical radii can result from the manufacturing process or from the in situ conformation of a spherical radii device of flexible materials. The edge lift radii of the peripheral curves 430 can range from 0.0 to 5.0 mm flatter than the base curve radii in each meridian. More preferred is 0.50 to 5.0 mm flatter than the base curve radii in each meridian. Most preferred is from 2.0 to 5.0 mm flatter than the base curve radii in each meridian. The peripheral curve 430 widths can range from 0.10 to 2.0 mm. More preferred is 0.10 to 1.0 mm. Most preferred is from 0.25 to 0.75 mm. The resulting edge profile incorporates the peripheral curvatures 430 of the anterior surface and the posterior surface of the device 400.

A contact lens design utilizes lid interaction during the blink and/or interblink period to optimally position the contact in relation to the cornea. As with a contact lens design, the most preferred embodiments of this invention have critical design features of anterior shape, edge contour and thickness profile that interact with the eyelid, both during and between blinks, to optimally orient the device in a stable and comfortable position, in this case on the sclera. An example of such a design feature of this invention that is well known in the art of contact lens design is that of the addition of a minus-carrier lenticular. This design feature affects the edge profile thickness and affects the interaction with the eyelid. This is known to aid in comfort as well as to stabilize and position the contact lens in the desired position on the eye. In a similar manner, the lenticular designs of our more preferred embodiments position and stabilize the ocular devices in the optimal position on the sclera. In fact, it can be observed in the art of contact lens practice that a rigid corneal contact lens with a minus carrier lenticular, if dislocated onto the superior sclera accidentally, tends to want to remain stable in that position. This is in spite of the other design features of the lens that would tend to have it return to the cornea. This interaction of a minus-carrier lenticular-type peripheral profile with the eyelid has been utilized in the most preferred embodiment of the present invention to optimize the position and stability of the device either in the superior or inferior position on the sclera. The more preferred embodiments utilize a lenticular on the lobes that is of larger radius than that of the central portion of the device. The lenticular radius is therefore smallest at the central vertical meridian of the device, with the distal (non-corneal) side lenticular radius at that point being closer to the larger lenticular radius of the lobes and having a larger (approximately double the size) radius than that of the proximal (corneal) side. In the preferred embodiments of the invention the lenticular is carried all the way around the perimeter of the device to assist in maintaining location of the device by the lid, balance of position and movement of the device with blinking, and minimal awareness of the device or foreign body sensation with lid movement. The lenticular radii for the distal (non-corneal side) central vertical meridian, proximal (corneal side) central vertical meridian and lobe range respectively from: preferred 0.0-5.0, 0.0-5.0, 0.0-5.0 mm; more preferred 0.5-3.5, 0.5-3.5, 0.5-3.5 mm; most preferred 1.0-2.0, 0.25-1.5, 1.5-2.5 min. The lenticular enhances balance and minimizes sensation of the device in interaction with the lid contact area. Stability and retention in the face of movement of the superior lid is particularly optimized with the use of a lenticular design.

The same elements of design resulting in the overall shape and surfaces and edge geometry of the embodiments of this invention allow the surgical placement of the device of this invention under the conjunctiva or Tenon's capsule for delivery of drug to the anterior or posterior of the eye 10. The overall shape of the preferred embodiments would fit into position anterior or posterior to a given extraocular muscle insertion. In the case of being placed posterior to a muscle insertion, the muscle relief curve would maintain its function, while the corneal relief curve would become an "optic nerve" relief curve. Primarily due to the curvatures on the anterior and posterior surfaces and the edge apex contour, there would be minimal structural interference with the tissues surrounding the device of this invention, during surgical insertion, wear and surgical removal, if necessary. The maximized volume of the device as described in each of the present embodiments allows delivery of significant quantities of drug in order to minimize the number of surgical replacements necessary, yet remain unobtrusive in the normal movements and sensations of the eye.

The present invention describes the design of an ocular device that overcomes the deficiencies associated with the conventionally designed ocular devices and incorporates one or more of the following features: (a) the ocular device is designed to fit the sclera of the eye; (2) the ocular device is designed to be retained on the eye independent of the eyelid; (3) the ocular device is designed to move and position with the blink; (4) the ocular device is designed such that the base curvature of the device is spherical, aspherical, or toric and is defined in relation to scleral anatomical geometry; (5) the ocular device employs one or more lobes to maximize the mass and volume; (6) the ocular device employs two lobes with greater mass and thickness than the central connecting portion (dumbbell shape); (7) the ocular device has a volume from about 70 µl to about 400 µl; (8) the ocular device has a length from about 8 mm to about 35 mm; (9) the ocular device has a height from about 1.0 mm to about 14 mm; (10) the ocular device has a thickness from about 0.10 mm to about 5.0 mm; (11) the ocular device has a defined edge apex contour; (12) the ocular device has a defined edge lift; (13) the ocular device has a defined front curve(s); (14) the ocular device has front curves that are toric; (15) the ocular device has front curves that are aspheric; and (16) the ocular device has a lenticular that is utilized on the front curve geometry.

The present invention can be made in considerably larger dimensions than is claimed by prior art, and yet still remain stable and comfortable. The consequent volume, shape features and intended use of the device design renders its insertion, in situ evaluation and removal intuitive to the ophthalmologist, optometrist, other contact lens practitioner, nurse, or ophthalmic technician. The present invention describes a device that does not need forceps or other instruments or surgical procedures for insertion or removal. Patients could be taught to insert and remove such a device, in the manner that they are taught to insert and remove contact lenses. This does not preclude the device from being placed underneath the conjunctiva or Tenon's capsule, for example, for drug delivery to the posterior segment of the eye, in which case surgical instruments would be involved in the procedure of device implantation.

In one preferred embodiment, the devices are made of non-erodable or erodable materials. Examples of non-erodable materials are, but are not limited to, polyacrylates and methacrylates, polyvinyl ethers, polyolefins, polyamides, polyvinyl chloride, fluoropolymers, polyurethanes, polyvinyl esters, polysiloxanes and polystyrenes. Examples of erodable materials are cellulose derivatives such as methylcellulose, sodium carboxymethyl cellulose, hydroxyethyl cellulose, hydroxypropyl cellulose and hydroxypropylmethyl cellulose; acrylates such as polyacrylic acid salts, ethylacrylates and polyacrylamides; natural products such as gelatin, collagen, alginates, pectins, tragacanth, karaya, chrondrus, agar and acacia; starch derivatives such as starch acetate, hydroxyethyl starch ethers and hydroxypropyl starch as well as synthetic derivatives such as polyvinylalcohol, poly vinylpyrrolidone, poly vinyl methyl ether, poly ethyleneoxide, neutralized Carbopol®, xanthan gum, polyester, poly ortho ester, poly anhydride, poly phosphazine, poly phosphate ester, poly caprolactone, poly hydroxybutyric acid, poly glycolic acid, poly lactic acid and combinations thereof.

In another embodiment of the present invention, there is provided a method of delivering a drug to the eye of an individual in need of such medication, comprising the steps of placing the drug into the drug delivery device and then contacting the individual with the drug-containing drug delivery device by placing the device on the inferior or superior sclera of the eye. A representative ocular disease is glaucoma; those skilled in the art will recognize other diseases, infections or inflammations of the eye that could be treated in this manner using this invention. The drug delivery devices of this invention may contain any of a variety of useful drugs, for glaucoma, allergy, infection, inflammation, uveitis, trauma, post-surgical prophylaxis, pain, dry eye or degenerative conditions. Other agents, such as lubricants, humectants, viscosifiers, demulcants or vitamins, may also be delivered with this invention.

In yet another embodiment of the present invention, there is provided a method of delivering a drug systemically to an individual in need of such medication, that includes the steps of: placing a drug with poor ocular absorption kinetics into the drug delivery device and then contacting the individual with the drug-containing drug delivery device by placing the device on the inferior or superior sclera of the eye so that the drug that is released travels with the tear drainage pathway into the naso-lacrimal duct and is absorbed systemically via the nasal mucosa and drainage pathway. A representative systemic disease is diabetes, and a representative drug is insulin; those skilled in the art will recognize other systemic diseases, infections or inflammations that could be treated in this manner using the present ocular devices.

In another embodiment of the present invention, there is provided a method of delivering a drug to the eye of an individual in need of such medication, comprising the steps of placing the drug into the drug delivery device and then contacting the individual with the drug-containing drug delivery device by placing the device on the inferior or superior sclera of the eye posterior to the superior or inferior rectus muscle insertions, below the conjunctiva, intermuscular membrane or Tenon's capsule, or even into the episcleral space. In this surgical implantation, the device would still provide a large volume in a shape corresponding to the anatomical potential space of insertion. Movement with eye movement would be limited and less necessary than for embodiments worn on the external eye. The posterior eye would be more accessible for drug penetration from this embodiment as placed. Representative ocular diseases are macular degeneration, posterior uveitis, endophthalmitis, diabetic retinopathy, glaucomatous neuropathy; those skilled in the art will recognize other diseases, infections or inflammations of the posterior eye that could be treated in this manner using this invention. The drug delivery devices of this invention may contain any of a variety of useful drugs, for glaucoma, retinopathy, infection, inflammation, uveitis, trauma, post-surgical prophylaxis or degenerative conditions. In another embodiment of the present invention, there is provided a method of delivering a drug systemically to an individual in need of such medication, comprising the steps of placing the drug into the drug delivery device and then contacting the individual with the drug-containing drug delivery device by placing the device on the inferior or superior sclera of the eye. A representative systemic disease is diabetes; those skilled in the art will recognize other diseases, infections or inflammations of the body that could be treated in this manner using this invention. The drug delivery devices of this invention may contain any of a variety of useful drugs, for diabetes, hypertension, cancer, arthritis, infection, inflammation, various autoimmune diseases, and other systemic pathologies that that those skilled in the art of drug delivery will recognize. Other and further aspects, features and advantages of the present invention will be apparent from the following description of the presently preferred embodiments of the invention given for the purpose of disclosure.

The devices of this invention can be fabricated from polymer based materials. The drug or medicinal agent can either be in a dissolved or dispersed state within this polymeric matrix. In one embodiment the drug or medicinal agent is compounded into a preformed polymer where it may be in the dissolved or dispersed state. The device is then formed form this drug containing polymer. Examples of useful polymer matrices are ethylene vinyl acetate and acrylic based polymer materials. In another embodiment, the drug or medicinal agent can be compounded into a reactive system. That system may be a monomer or macromer where the drug or medicinal agent is in the dissolved or dispersed state. Polymerizing the system through UV, visible light, heat or a combination of these means then forms the device. Examples would include the use of liquid acrylic monomers or a reactive silicone pre-polymer.

A preferred manufacturing process for producing the drug delivery devices of this invention is cast molding. In this process a drug is dissolved or dispersed in a monomer mixture and placed in a plastic casting mold bearing the geometry of the ocular device. Thermal exposure, UV exposure or a combination of both polymerizes the monomer. The device is then removed from the mold. Post processing may be required, for example edge finishing. In the case of an ocular device polypropylene casting molds are preferred. Most preferred is a polypropylene resin with a melt flow index above 20. One polypropylene resin is Exxon PP1105E, which has a melt flow index of 34 g/10 min. With melt flows above 20 gm/10 min intricately shaped casting molds can be injection molded with excellent replication of part dimensions.

Post processing is oftentimes required to remove flash and/or to contour the parting line. For an ocular device, such as contact lenses and the devices of this invention, the edge profile is critical in providing device comfort and fit. The edges of the ocular devices of this invention can be shaped and contoured utilizing standard polishing techniques currently available for rigid gas permeable contact lenses. More preferred is the use of laser edging to form a smooth, well-contoured edge.

Example 1

Figure 6:
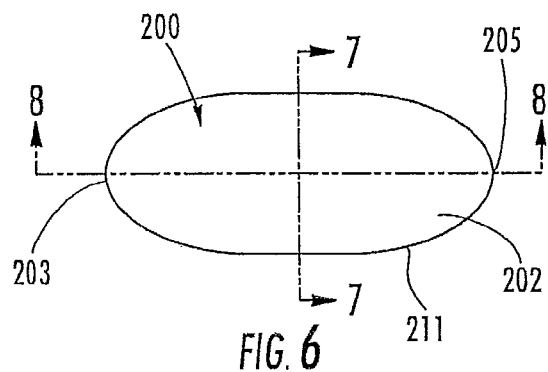
FIG. 6 is a front elevation view of an ocular drug delivery device according to a second embodiment.
Figure 7:
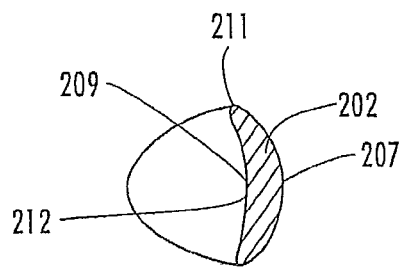
FIG. 7 is a cross-sectional view taken along the line 7-7 of FIG. 6.

The aspects of the device of Example One are shown in FIGS. 6-8. The overall shape of this invention is greater horizontally than vertically, and can appear as an oval in as shown in the front elevation view of FIG. 6. It is preferred that the shape be symmetrical about the vertical meridian, such that the lateral halves are mirror images. This aspect allows for the same device design to be used in the right and left eyes (in the same orientation), and on the superior or inferior sclera of an eye. The base curve 114 radius is chosen to fit the sclera 50. The center thickness is greatest in the horizontal centerline, with tapering to a defined minimal, mostly uniform edge thickness around the entire edge perimeter of the ellipse where the anterior surface 207 and posterior surface, 209 meet. This entails a significantly tone shape on a fairly spherical base curve with a uniform edge radius. Size can range from about 10 mm to about 25 mm in width by about 5 mm to about 12 mm in ht by about 1.0 mm to about 3.0 mm center thickness. The base curve radius 114 is from about 10 mm to about 20 mm. The volume of the device ranges from about 70 μl to about 400 μl. A device in accordance with FIGS. 6-7 was constructed from a silicone elastomer. The dimensions were 16 mm in width, 7.0 mm in height and 2.3 mm in center thickness, which tapered down from the center point. The toric front surface radii were 4.0 mm vertical meridian by 9.0 mm horizontal meridian. The base curve radius was 12.4 mm. The device volume was 150 μl.

Example 2

The aspects of the device of Example two are shown in FIGS. 6-8. The general geometric parameters were discussed in Example One. A prototype device was constructed from silicone elastomer. The overall width was 21.0 mm, the height was 7.8 mm and the center thickness was 1.5 mm. The tonic front surface radii were 5.0 mm vertical meridian and 12.0 mm horizontal meridian. The base curve radius was 12.4 mm. The overall device volume was 150 μl. This device was placed on the superior sclera of a subject's eye. The device was stable in the eye with slight rotation observed. The comfort of the device was reported to be good.

Example 3

The aspects of the device of Example Three are shown in FIGS. 6-8. The general geometric parameters were discussed in Example One. A prototype device was constructed from silicone elastomer. The overall width was 24.5 mm, the height was 10.0 mm, and the center thickness was 2.3 mm. The toric front surface radii were 6.0 mm vertical meridian by 12.5 mm horizontal meridian. The overall device volume was 385 µl.

The device was placed on the superior sclera of a subject's eye. The device tended to move slightly to a nasal position. The comfort was rated at "slight awareness".

Example 4

The aspects of the device of Example Four are shown in FIGS. 9-12. The overall shape is a horizontal "dumbbell" symmetrical about both the central vertical axis and the central horizontal axis. A prototype device that included the lenticular feature on the anterior geometry of the lobes was constructed from silicone elastomer. The distance between the anterior and posterior surfaces, center thickness, (midway between the lobes) was 0.75 mm. The distance between the two surfaces at the center of each lobe was 1.5 mm. The anterior curvature at the center of the lobe was 4.3 positive radius, transitioning to 2.0 mm negative lenticular radius and then transitioning to a 0.25 positive edge radius. Overall width was 20.5 mm Vertical height was 8.45 mm at its maximum at each lobe, and 6.5 mm at the center of the device. The back curve radius was approximately 12.4 mm. Volume was 130 µl. The lobes could be detected (cosmetically visible) as slight elevations of the eyelid. The device with the lenticular demonstrated clinically acceptable position, stability and retention, both in the superior and inferior positions. Comfort was quite good, with the exception of some sensation of the edge.

Example 5

The aspects of the device of Example Five are shown in FIGS. 13-15. A prototype device was made that was overall higher and wider than Example 4. This device was 21 mm wide and 7.25 mm height in the center of the device. This dumbbell version was 9.5 mm in the dumbbell lobe height as viewed from the front. A uniform spherical 12.4 mm back curvature was used, as the material used was quite flexible. The indentation distal to the cornea yielded a 0.26 mm maximum differential in height of the device due to this curvature. Device was 2.77 mm from the horizontal meridian running through the center of the peripheral lobes to the edge of the device proximal to the cornea. The same measurement from the horizontal meridian (running through the center of the peripheral lobes) to the edge was 4.47 mm on the side distal to the cornea. We increased the front negative lenticular curvature to 2.1 mm. The actual true radius was therefore 4.0 mm. We smoothed over the transition curves to make the "bumps" of the lobes less visible under the upper lid during wear. The width is slightly greater as well. The anterior edge radius was decreased, bringing it more into the realm of a contact lens radius but the edge lift was the same. The tighter radius is an attempt to lessen the edge sensation from the upper lid, to increase comfort. Volume was 136 µl.

On eye, this device was the most comfortable yet in the superior position. No "bumps" were visible under the superior lid. It felt very stable in its interaction the lid. Removal was still relatively easy to accomplish by massaging the device downward via external manual manipulation of the eyelid and then removing the device manually, as is done with a contact lens, once it became visible in the palpebral aperture.

Example 6

The aspects of the device of Example Six are shown in FIGS. 13-15. A prototype device was cast-molded from an acrylic monomer, with increased edge lift compared to Example 5 due to the addition of a secondary peripheral curve radius. This device was 21 mm wide and 7.25 mm in height in the center of the device. This embodiment was 9.45 mm in the height of the lobe sections as viewed from the front. The horizontal front curve is a spline that smoothly blends the center and lobe regions that have defined vertical front curve radii and edge lift radii and widths. The front curvature radius in the center axis 15-15 was 7.26 mm centrally, and 5.09 mm at the lobes. The indentation proximal to the cornea was cut at a lenticular radius of 0.75 mm and yielded a 1.95 mm maximum differential in height of the device due to this curvature. The device was 2.77 mm from the axis 14-14 running through the center of the peripheral lobes to the edge of the device proximal to the cornea. The indentation distal to the cornea was cut at a lenticular radius of 1.50 mm and yielded a 0.26 mm maximum differential in height of the device due to this curvature. The device was 4.47 mm from the axis 14-14 running through the center of the peripheral lobes to the edge of the device distal to the cornea. The lenticular reverse curve of the lobe was 2.1 mm. The width of the lenticular curve was 1.13 mm proximal to the cornea and 1.23 distal to the cornea. The edge apex radius was 0.56 mm with an edge thickness of 0.43 mm. A toric-12.4 mm vertical meridian (axis 15-15), 12.5 mm horizontal meridian (axis 14-11)—back curvature was used since the material was quite flexible. The edge lift base curve radius was 16.4 mm, with a width of 1.0 mm, in the vertical meridian centrally (15-15), and 16.4 mm, with a width of 1.2 mm, along the entire periphery at the lobes. The volume was 124 µl. The ocular device of this Example 6 was cast-molded from an acrylic monomer formulation as follows. The design of the device was machined into metal molds. Casting mold halves were injection molded from Exxon polypropylene PP1105E. Under an inert atmosphere the lower casting mold half was filled with an acrylic monomer formulation containing a UV initiator. The upper casting mold half was fitted into the lower casting mold half to form the device shape. The closed casting mold assembly was placed in a UV curing chamber and exposed to UV at wavelength 365 nm for thirty minutes. The polymerized ocular device was then removed. A peripheral curve system was molded into the posterior periphery of the device. Their width and their incremental increases in radius values define these peripheral curves over the central base curves. In one embodiment, these values for each curve can be uniform around the peripheral posterior surface of the device. Our most preferred peripheral curve system comprises curves of different widths in the central and lateral lobe parts of the device. The peripheral curve system provides the edge lift. This approach is utilized in the contact lens art to enhance comfort, movement and tear film exchange. When placed on a subject, the device of this Example 6 performed as well as that of Example 6 in all aspects, with the additional results of having increased comfort with little or no sensation of the device in the eye. Lag with eye movement, and movement and repositioning with blink, were excellent. Utilizing a fluorescent dye, a peripheral band of dye under the device, corresponding to the peripheral curve system and its associated edge lift, could be observed in a manner consistent with standard clinical evaluation of such an observation of rigid contact lenses. The width, evenness, and intensity of this band of fluorescent dye, relative to the fluorescent intensity under the rest of the device, was judged to be clinically excellent using criteria practiced by one skilled in rigid contact lens clinical practice. All of the designs and methods disclosed and claimed herein can be made and executed without undue experimentation in light of the present disclosure. While, the designs and methods of this invention have been described in terms of preferred embodiments, it will be apparent to those skill in the art that variations may be applied to the designs and/or methods and in the steps or in the sequence of steps of the methods described herein without departing from the concept, spirit and scope of the invention. All such similar substitutes and modifications apparent to those skilled in the art are deemed to be within the spirit, scope and concept of the invention as described by the appended claims.

What is claimed is:

1. An ocular device for delivery of a therapeutic agent to the eye comprising:
    a preformed body having an anterior surface and an opposite posterior surface for placement on the sclera of the eye, the posterior surface having a preformed concave curved shape outside of the eye that is defined by a base curve shaped to fit the sclera;
    wherein the preformed body is configured to be held on the sclera such that the preformed body is free of contact with and spaced from a cornea of the eye.

2. The ocular device of claim 1, wherein the posterior surface includes a first section that is defined by the base curve and an adjacent second section at peripheral edges of the body that is defined by edge lift radii; wherein the posterior surface is shaped to fit the sclera of the eye so as to permit the device to be held on the eye by fluid attraction and be retained on the eye without aid of an eyelid.

3. The ocular device of claim 1, wherein the body includes a central portion with a first edge that faces the cornea of the eye when the body is placed on the sclera, the first edge having an inwardly curved shape.

4. The ocular device of claim 3, wherein the first edge has a shape corresponding approximately to a projection of a corneal perimeter.

5. The ocular device of claim 3, wherein the central portion includes a second edge, opposite the first edge, that is further from the cornea when the body is placed on the sclera, the second edge having an inwardly curved shape, the curvature of the second edge being different than the curvature of the first edge.

6. The ocular device of claim 1, wherein the preformed body of the ocular device is constructed to be held on a tear film of the sclera by fluid attraction and maintained in a held state thereon such that the preformed body remains free of contact with and spaced from the cornea.

7. The ocular device of claim 1, wherein the posterior surface is configured for placement on one of a superior sclera and inferior sclera of the eye.

8. An ocular device for delivery of a therapeutic agent to the eye comprising:
    a preformed elongated body having an anterior surface and an opposite posterior surface for placement on the sclera of the eye, the posterior surface having a preformed curved shape outside of the eye that is shaped to fit the sclera, wherein curvature of the posterior surface extends along a longitudinal length of the preformed elongated body;
    wherein the preformed body has one or more lobes, each lobe having a horizontal width and height greater than a horizontal width and height, respectively, of a peripheral edge of the preformed body, wherein the increased size of the lobe maintains positioning and stability of the preformed body on the eye through interaction with an eyelid of the eye.

9. An ocular device for delivery of a therapeutic agent to the eye comprising:
    a preformed elongated body having an anterior surface and an opposite posterior surface for placement on the sclera of the eye, the posterior surface having a preformed curved shape outside of the eye that is defined by a base curve shaped to fit the sclera, wherein the curvature extends in a longitudinal direction of the elongated body such that the posterior surface of the elongated body has concave curvature along its length prior to insertion into the eye;
    wherein the preformed body is configured to be held on the sclera such that the preformed body is free of contact with and spaced from a cornea of the eye.

* * * * *